(12) United States Patent
Alyassin et al.

(10) Patent No.: US 7,313,259 B2
(45) Date of Patent: Dec. 25, 2007

(54) METHOD, SYSTEM AND COMPUTER PROGRAM PRODUCT FOR MULTI-MODALITY REGISTRATION USING VIRTUAL CURSORS

(75) Inventors: Abdalmajeid M. Alyassin, Niskayuna, NY (US); Ajay Kapur, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 722 days.

(21) Appl. No.: 10/722,640

(22) Filed: Nov. 26, 2003

(65) Prior Publication Data
US 2006/0159318 A1 Jul. 20, 2006

(51) Int. Cl.
*G06K 9/00* (2006.01)
(52) U.S. Cl. ......................... 382/128; 382/284; 382/294
(58) Field of Classification Search ................. 382/128; 600/407
See application file for complete search history.

(56) References Cited

U.S. PATENT DOCUMENTS

| | | |
|---|---|---|
| 3,971,950 A | 7/1976 | Evans et al. |
| 4,407,163 A | 10/1983 | Hundt et al. |
| 4,509,368 A | 4/1985 | Whiting et al. |
| 4,543,959 A | 10/1985 | Sepponen |
| 4,936,291 A | 6/1990 | Forssmann et al. |
| 5,474,072 A | 12/1995 | Shmulewitz |
| 5,479,927 A | 1/1996 | Shmulewitz |
| 5,581,180 A | 12/1996 | Ito et al. |
| 5,603,326 A | 2/1997 | Richter |
| 5,630,426 A | 5/1997 | Eggers et al. |
| 5,640,956 A | 6/1997 | Getzinger et al. |
| 5,660,185 A | 8/1997 | Shmulewitz et al. |
| 5,664,573 A | 9/1997 | Shmulewitz |
| 5,735,264 A | 4/1998 | Siczek et al. |
| 5,776,062 A | 7/1998 | Nields |
| 5,803,082 A | 9/1998 | Stapleton et al. |
| 5,810,742 A | 9/1998 | Pearlman |
| 5,820,552 A | 10/1998 | Crosby et al. |

(Continued)

OTHER PUBLICATIONS

U.S. Appl. No. 10/265,489, filed Oct. 7, 2002—Continuous Scan Tomosynthesis System and Method.

(Continued)

*Primary Examiner*—Bhavesh M Mehta
*Assistant Examiner*—John B Strege
(74) *Attorney, Agent, or Firm*—Fletcher Yoder

(57) ABSTRACT

A method for multi-modality registration using virtual cursors including receiving a two-dimensional image dataset for an object at a first position and receiving a three-dimensional image dataset for the object at the first position. The three-dimensional image dataset includes a plurality of image slices. The two-dimensional image dataset is registered with the three-dimensional image dataset without taking into account a magnification factor. A user cursor position for a location in the two-dimensional image dataset is received. A slice of interest in the three-dimensional image dataset is received. The slice of interest is selected from the plurality of image slices in the three-dimensional image dataset. A shadow cursor position for a location in the three dimensional dataset is calculated. The shadow cursor position corresponds to the user cursor position and the calculating includes a correction for the magnification factor corresponding to the shadow cursor position for the slice of interest. The shadow cursor position is output.

20 Claims, 7 Drawing Sheets

U.S. PATENT DOCUMENTS

| | | |
|---|---|---|
| 5,828,774 A | 10/1998 | Wang |
| 5,840,022 A | 11/1998 | Richter |
| 5,851,180 A | 12/1998 | Crosby et al. |
| 5,855,554 A | 1/1999 | Schneider et al. |
| 5,938,613 A | 8/1999 | Shmulewitz |
| 5,983,123 A * | 11/1999 | Shmulewitz ............. 600/407 |
| 5,984,870 A | 11/1999 | Giger et al. |
| 5,999,639 A | 12/1999 | Rogers et al. |
| 6,611,575 B1 | 8/2003 | Alyassin et al. |
| 7,103,205 B2 * | 9/2006 | Wang et al. ............. 382/132 |
| 2003/0149364 A1 | 8/2003 | Kapur et al. |
| 2003/0167004 A1 * | 9/2003 | Dines et al. ............. 600/437 |
| 2003/0194050 A1 | 10/2003 | Eberhard et al. |
| 2003/0194121 A1 | 10/2003 | Eberhard et al. |

OTHER PUBLICATIONS

U.S. Appl. No. 10/692,450, filed Oct. 23, 2003—Systems and Methods for Viewing an Abnormality in Different Kinds of Images.
U.S. Appl. No. 10/723,318, filed Nov. 25, 2003—Compression Paddle Membrane and Tensioning Apparatus for Compressing Tissue for Medical Imaging Purposes.

* cited by examiner

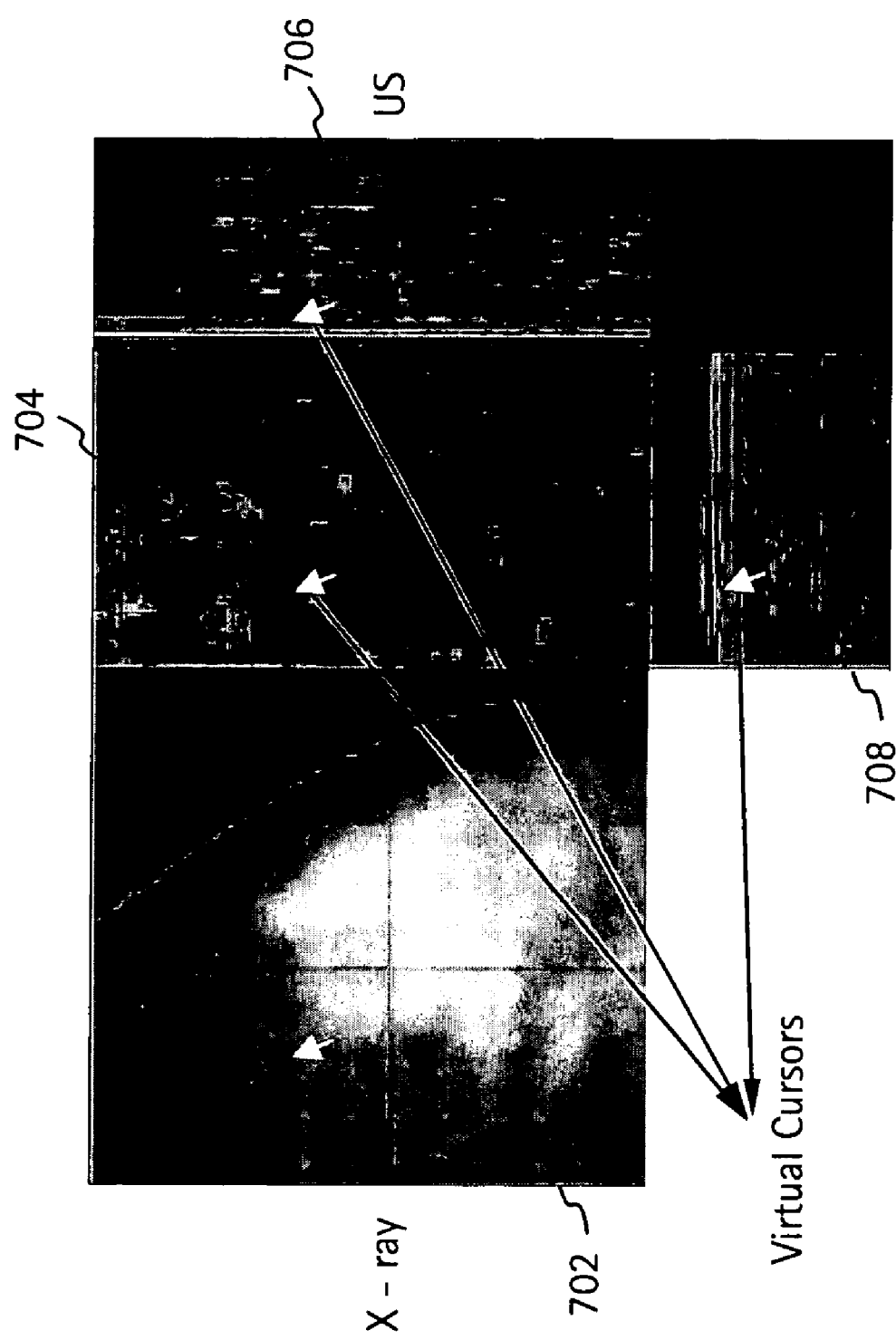

METHOD, SYSTEM AND COMPUTER PROGRAM PRODUCT FOR MULTI-MODALITY REGISTRATION USING VIRTUAL CURSORS

STATEMENT REGARDING FEDERALLY SPONSORED RESEARCH AND DEVELOPMENT

The government may have rights in this invention pursuant to Subcontract 22287 issued from the Office of Naval Research/Henry M. Jackson Foundation.

BACKGROUND OF THE INVENTION

The present disclosure relates generally to multi-modality registration and, more particularly, to a method of using virtual cursors to show pixel-to-pixel correspondence between multi-modality datasets.

Recently, multi-modality acquisitions in the medical imaging field have become more common. Different modalities have different strengths and may provide unique diagnostic information. For example, when performing mammograms, ultrasound is particularly effective at differentiating benign cysts and masses while x-ray is typically used for detailed characterization of microcalcifications. Combining the images generated using an x-ray detector with with the images generated using an ultrasound system leverages the strengths of both modalities. However, one of the challenging aspects is how to spatially register these modality datasets, such that there is a one to one pixel/voxel correspondence while preserving the quality of the original scanned data. One of the challenges in registering 2D x-ray data to 3D ultrasound data is the magnification factor in the projected 2D x-ray data. This factor is calculated based on the spatial relationship between the x-ray source, the scanned object and the image receptor. Registering 3D ultrasound data to 2D x-ray data requires corrections for the magnification factor of the x-ray data in every 3D ultrasound slice because ultrasound data does not contain a magnification factor. Scaling the ultrasound data to account for the magnification factor increases the size of the ultrasound data and may produce or change the normal look of the ultrasound data. The result of scaling the ultrasound image data is that the ultrasound data may have an appearance that looks different than the standard view that mammographers and radiologists are accustomed to viewing and analyzing. This may be especially pronounced when the x-ray source is not centered on the image receptor as is the case during the x-ray to ultrasound mammography data acquisition.

BRIEF DESCRIPTION OF THE INVENTION

In one aspect, a method for multi-modality registration using virtual cursors includes receiving a two-dimensional image dataset for an object at a first position and receiving a three-dimensional image dataset for the object at the first position. The three-dimensional image dataset includes a plurality of image slices. The two-dimensional image dataset is registered with the three-dimensional image dataset without taking into account a magnification factor. A user cursor position for a location in the two-dimensional image dataset is received. A slice of interest in the three-dimensional image dataset is received. The slice of interest is selected from the plurality of image slices in the three-dimensional image dataset. A shadow cursor position for a location in the three dimensional dataset is calculated. The shadow cursor position corresponds to the user cursor position and the calculating includes a correction for the magnification factor corresponding to the shadow cursor position for the slice of interest. The shadow cursor position is output.

In another aspect, a method for multi-modality registration using virtual cursors includes receiving a two-dimensional image dataset for an object at a first position and receiving a three-dimensional image dataset for the object at the first position. The three-dimensional image dataset includes a plurality of image slices. The two-dimensional image dataset is registered with the three-dimensional image dataset without taking into account a magnification factor. A slice of interest in the three-dimensional image dataset is received. The slice of interest is selected from the plurality of image slices. A user cursor position for a location in the slice of interest in the three-dimensional image dataset is received. A shadow cursor position for a location in the two-dimensional image dataset is calculated. The shadow cursor position corresponds to the user cursor position and the calculating includes a correction for the magnification factor corresponding to the shadow cursor position. The shadow cursor position is output.

In still another aspect, a system for multi-modality registration using virtual cursors includes a computer system in communication with a first imaging system and a second imaging system. The first imaging system creates a two-dimensional image dataset for an object at a first position and the second imaging system creates a three-dimensional image dataset of the object at the first position. The three-dimensional image dataset includes a plurality of image slices. The computer system includes instructions to implement a method comprising receiving the two-dimensional image dataset from the first imaging system and receiving the three-dimensional image dataset from the second imaging system. The two-dimensional image dataset is registered with the three-dimensional image dataset without taking into account a magnification factor. A user cursor position for a location in the two-dimensional image dataset is received. A slice of interest in the three-dimensional image dataset is received. The slice of interest is selected from the plurality of image slices in the three-dimensional image dataset. A shadow cursor position for a location in the three dimensional dataset is calculated. The shadow cursor position corresponds to the user cursor position and the calculating includes a correction for the magnification factor corresponding to the shadow cursor position for the slice of interest. The shadow cursor position is output.

In a further aspect, a computer program product for multi-modality registration using virtual cursors comprises a storage medium readable by a processing circuit and storing instructions for execution by the processing circuit for performing a method. The method comprises receiving a two-dimensional image dataset for an object at a first position and receiving a three-dimensional image dataset for the object at the first position. The three-dimensional image dataset includes a plurality of image slices. The two-dimensional image dataset is registered with the three-dimensional image dataset without taking into account a magnification factor. A user cursor position for a location in the two-dimensional image dataset is received. A slice of interest in the three-dimensional image dataset is received. The slice of interest is selected from the plurality of image slices in the three-dimensional image dataset. A shadow cursor position for a location in the three dimensional dataset is calculated. The shadow cursor position corresponds to the user cursor position and the calculating includes a correction for the magnification factor corresponding to the shadow cursor position for the slice of interest. The shadow cursor position is output.

BRIEF DESCRIPTION OF THE DRAWINGS

Referring to the exemplary drawings wherein like elements are numbered alike in the several Figures:

FIG. 7 is a sample display of an x-ray image next to an ultrasound image in accordance with exemplary embodiments of the present invention.

DETAILED DESCRIPTION OF THE INVENTION

Disclosed herein is a multi-modality registration technique using virtual cursors with rigid registration. Utilizing exemplary embodiments of the present invention, x-ray data and ultrasound data may be registered to each other, including taking into account a magnification factor, while keeping the original data size and preserving the normal appearance of the two modalities of data. The virtual cursor registration technique eliminates the need to scale up the acquired data, thus reducing the required memory to handle large amounts of data. This speeds up the multi-modality registration. In addition the virtual cursor registration technique retains the data as it was acquired and therefore keeps the natural appearance of the data. Exemplary embodiments of the present invention may be utilized with multi-modality mammography as well as any other multi-modality imaging technologies where translation between the multiple modalities is desired.

Figure 1:
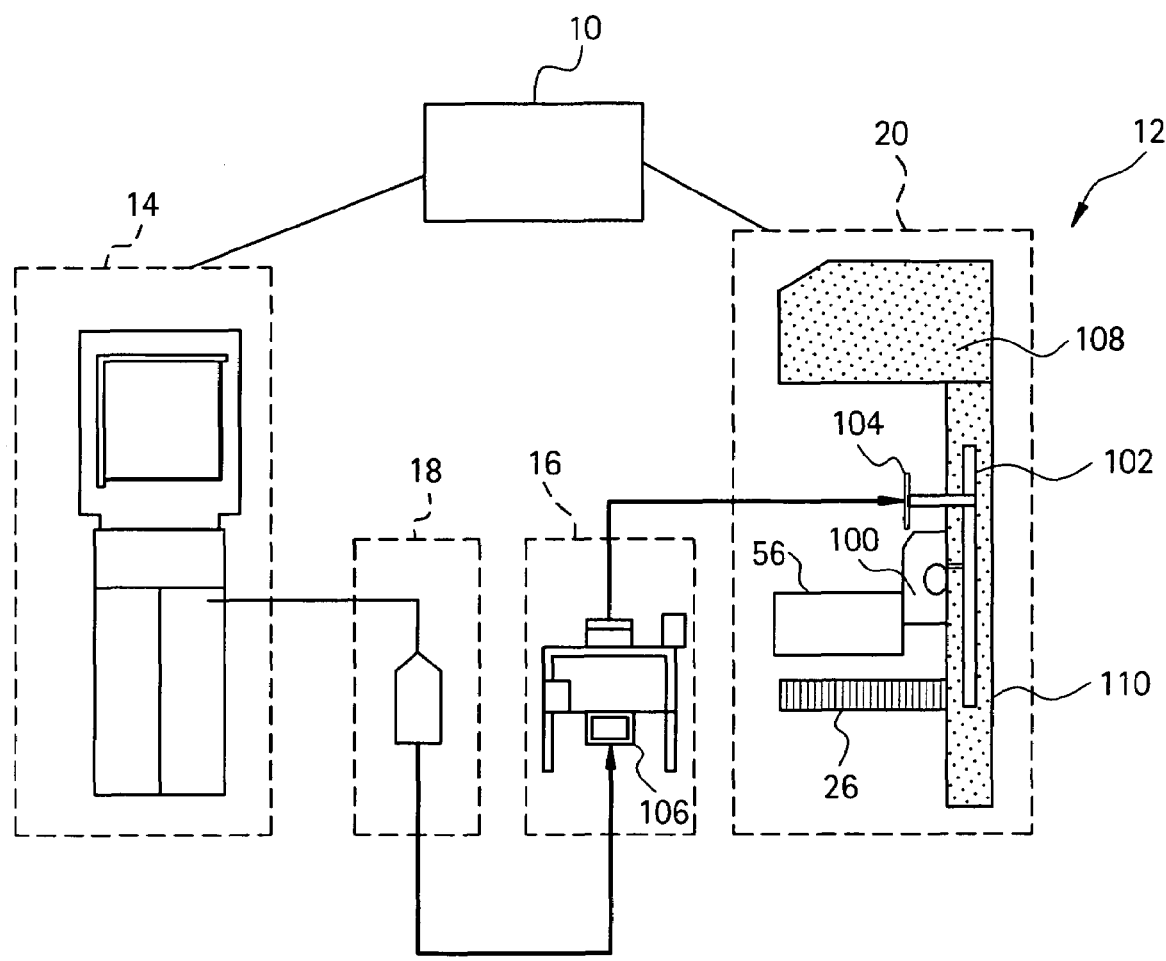
FIG. 1 is a pictorial view of a medical imaging system for performing multi-modality imaging.

FIG. 1 is a pictorial view of a medical imaging system 12 for performing multi-modality imaging. Image data collected by the medical imaging system 12 may be input to exemplary embodiments of the present invention for simultaneous viewing. In an exemplary embodiment of the present invention, the imaging system 12 includes an ultrasound imaging system 14, a probe mover assembly 16, an ultrasound probe 18, and an x-ray imaging system 20. The ultrasound imaging system 14, probe mover assembly 16, ultrasound probe 18 and x-ray imaging system 20 may be operationally integrated in the imaging system 12 or they may be physically integrated in a unitary imaging system 12. FIG. 1 also includes a compression paddle 56 that is installed in the x-ray imaging system 20 through a compression paddle receptacle 100. The probe mover assembly 16 may be attached to a receptacle (not shown) on a plurality of guide rails (not shown) on an x-ray positioner 102, above the compression paddle receptacle 100 through an attachment 104. Alternatively, the probe mover assembly 16 may be attached using a plurality of side handrails on the x-ray imaging system 20. As depicted in FIG. 1, the ultrasound probe 18 is connected to the ultrasound imaging system 14 on one end, and interfaces with the probe mover assembly 16 through a probe receptacle 106. In addition, the imaging system depicted in FIG. 1 includes an x-ray tube housing 108 and a radiation source 110. When FIG. 1 is utilized for mammography, a patient is placed adjacent the x-ray imaging system 20 with a breast positioned between compression paddle 56 and detector 26.

The ultrasound probe 18 and the probe mover assembly 16 geometry are calibrated with respect to the compression paddle 56. In one embodiment, calibrating the ultrasound probe 18 includes ensuring that the ultrasound probe 18 is installed into the probe mover receptacle 104, and that probe mover assembly 16 is attached to the x-ray imaging system 20 through the compression paddle receptacle 100. Calibrating the imaging system 12 facilitates ensuring that the transformation operations between coordinate systems are validated. The calibrating may be utilized to perform a mechanical registration between the different image modalities produced by the system depicted in FIG. 1. A correct beam-forming code environment is installed on ultrasound imaging system 14 to facilitate correcting refractive effects through compression paddle 56. Optimal parameters are then determined based on a prior knowledge of the patient or previous x-ray or ultrasound examinations.

The patient is positioned in a cranio-caudal, medial-lateral, or oblique position, such that the object of interest (e.g., a breast) is positioned between the compression paddle 56 and the detector 26. The compression paddle 56 is then used to compress the object of interest to an appropriate thickness using at least one of a manual control on the receptacle 100 and an automatic control for receptacle 100. X-rays for the object of interest are then taken by the x-ray imaging system 20 operating in a standard 2D mode. The results of the x-rays are stored in an x-ray image dataset and/or displayed on a device in communication with the x-ray imaging system 20.

The ultrasound probe 18, vertically mounted above compression paddle 56, is electro-mechanically scanned over the entire object of interest to generate a 3D dataset of the object of interest. The real time ultrasound data may be viewed on a monitor of the ultrasound imaging system 14 or on any display in communication with the ultrasound imaging system 14. In addition, the volumetric ultrasound data may be stored in an ultrasound image dataset.

FIG. 1 also includes a computer system 10 in communication with the ultrasound imaging system 14 and the x-ray imaging system 20. Communication may be via any network known the art (e.g., Internet, local area network). In an alternate exemplary embodiment of the present invention, the computer system 10 is physically located within the imaging system 12 and a network may not be required for communication. The computer system 10 includes instructions for performing the processing described in reference to FIGS. 4 and 5 and may include storage for the image data produced by the ultrasound imaging system 14 and/or the x-ray imaging system 20. Any kind of computer system known in the art (e.g., personal computer, integrated circuit module, host computer) may be utilized by exemplary embodiments of the present invention.

Figure 2:
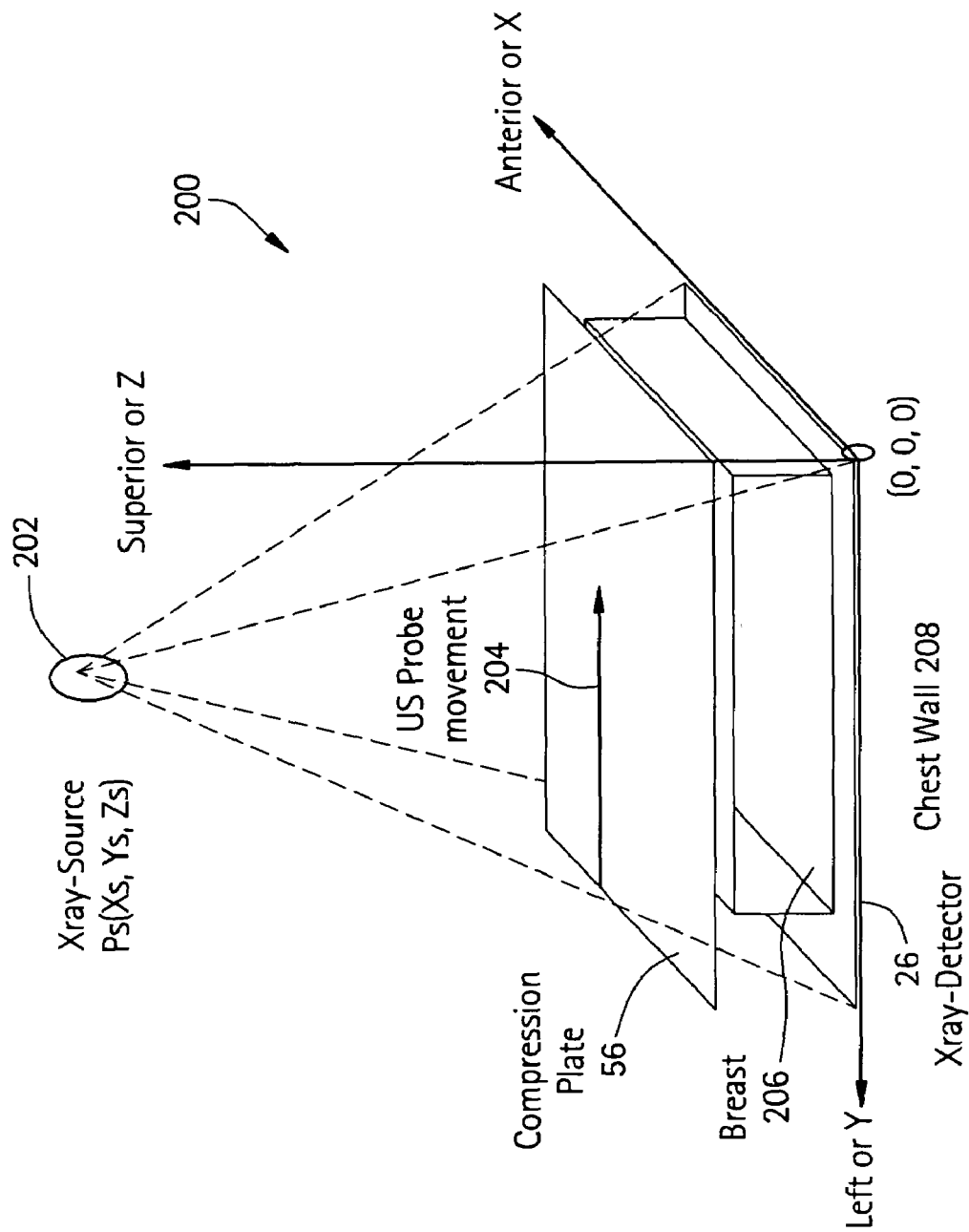
FIG. 2 depicts a reference coordinate system utilized by exemplary embodiments of the present invention.

FIG. 2 depicts a reference coordinate system utilized by exemplary embodiments of the present invention. The reference coordinate system is the coordinate system being utilized by exemplary embodiments of the present invention as the base coordinate system for use in creating the correspondence between image datasets of different modalities. FIG. 2 includes a coordinate location for the x-ray source 202, which may be expressed in the reference coordinate system as Ps(Xs, Ys, Zs), where Zs is always the same value because the x-ray image is 2D and therefore, the plane being covered is constant. FIG. 2 also shows the direction of the ultrasound probe movement 204, the compression plate 56, the placement of the object of interest (e.g., a breast) 206, the location of the patient's chest wall 208, and the location of the x-ray detector 26 all relative to the reference coordinate system. The reference coordinate system includes superior ("S" or "z"), anterior ("A" or "x") and left ("L" or "y") coordinates to specify locations in the reference coordinate system.

Figure 3:
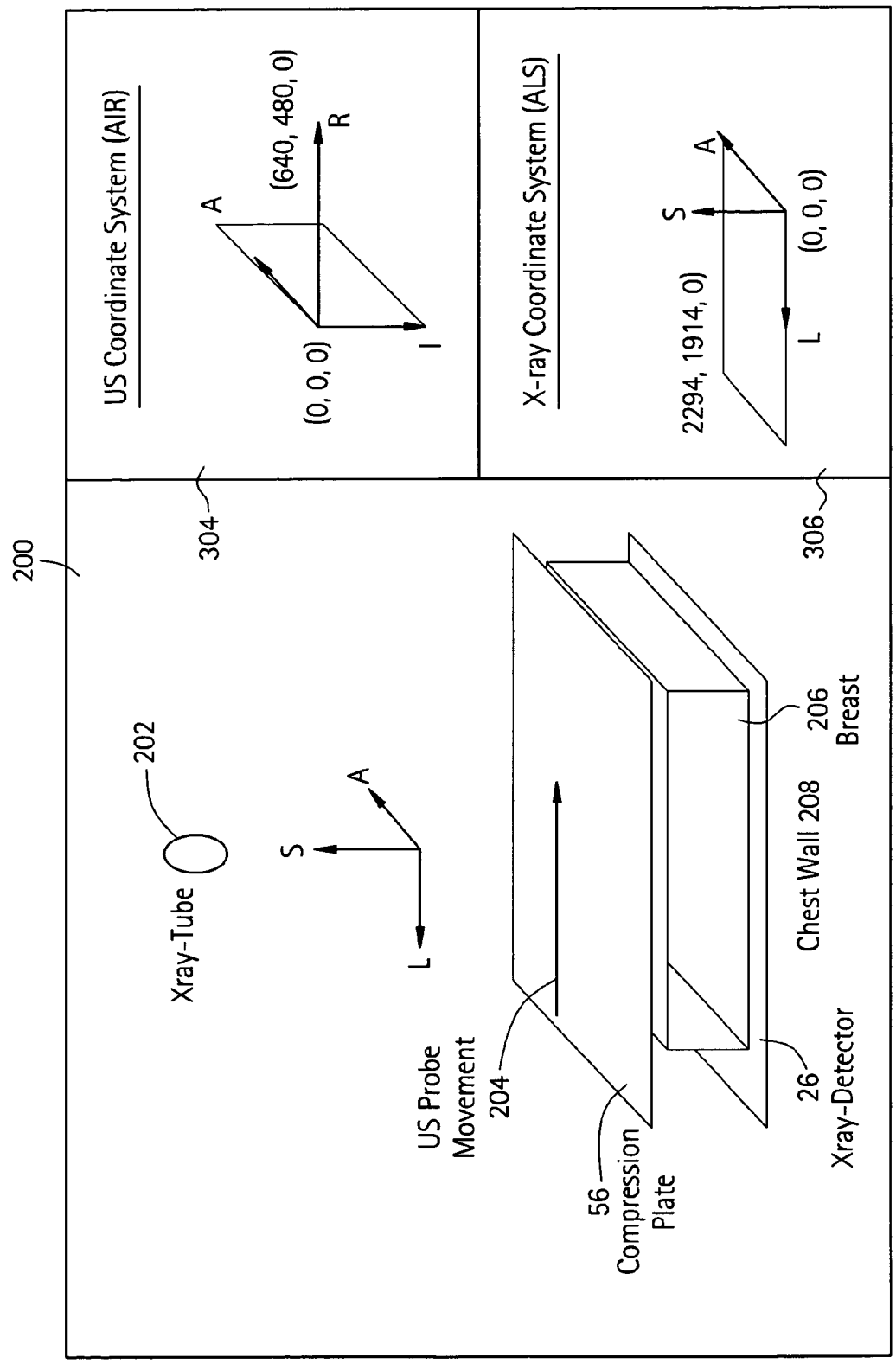
FIG. 3 depicts x-ray and ultrasound coordinate systems.

FIG. 3 depicts an anterior left superior (ALS) x-ray coordinate system and an anterior inferior right (AIR) ultrasound coordinate system relative to the reference coordinate system 200 depicted in FIG. 2. In addition, FIG. 3 depicts the ALS x-ray coordinate system and AIR ultrasound coordinate system relative to the ultrasound and x-ray imaging systems. The ultrasound coordinate system 304 depicted in FIG. 3 includes anterior ("A"), right ("R") and inferior ("I") coordinates for each voxel in the ultrasound image dataset. The x-ray coordinate system 306 depicted in FIG. 3 is expressed in terms of the same coordinate system as the reference coordinate system 200.

Figure 4:
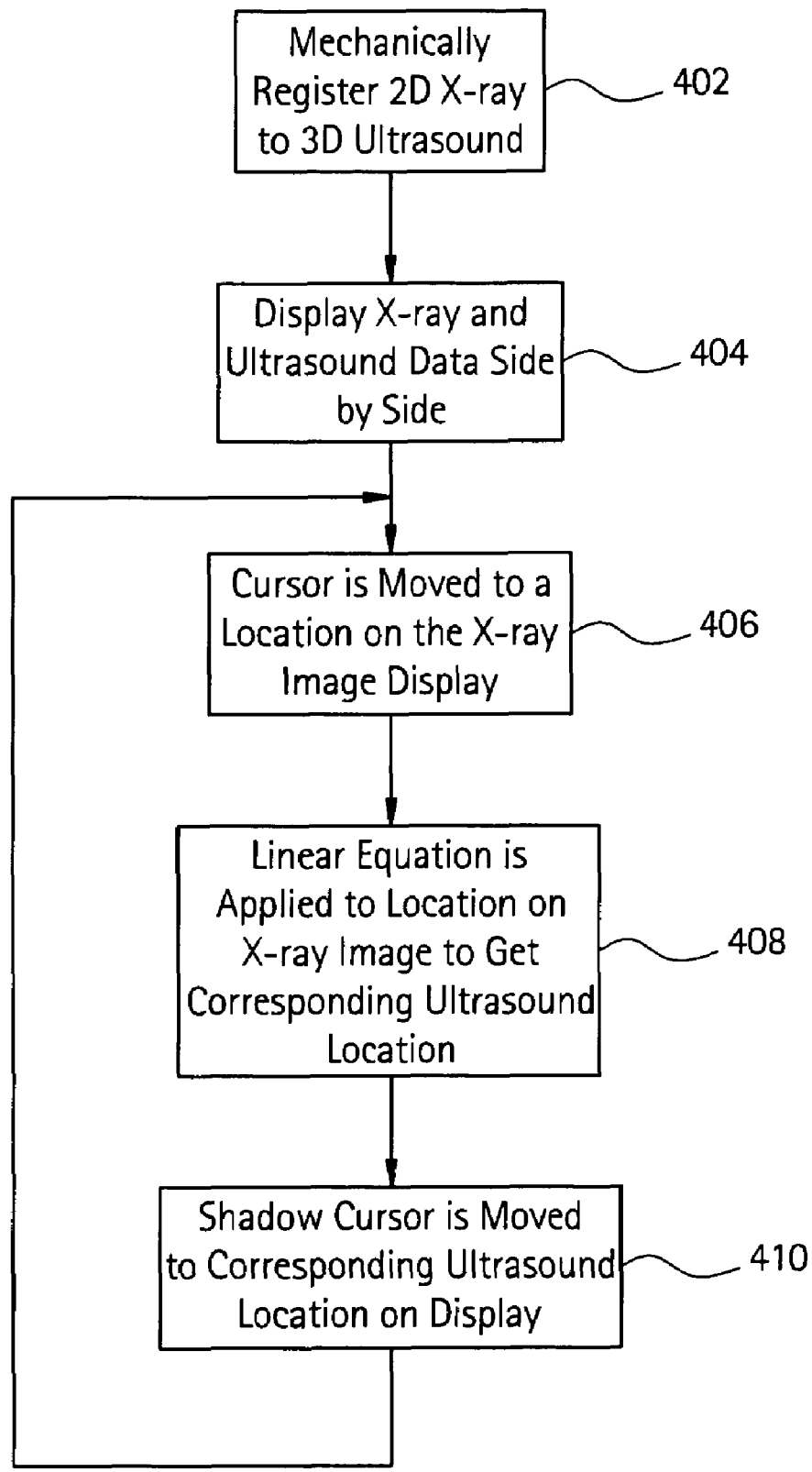
FIG. 4 is a flow diagram of an exemplary process for creating a shadow cursor.

FIG. 4 is a flow diagram of an exemplary process for creating a shadow, or virtual, cursor. At step 402, the 2D x-ray image dataset is mechanically registered to the 3D ultrasound image dataset. This preliminary registration process at step 402 does not account for the magnification factor in the x-ray image data. The registration process may include a mechanical registration, as is known the art, to obtain acquisitions coordinate system for both dataset and how they transform into each other. The mechanical registration process may be used if the datasets have been acquired at the same time. If the subject is scanned at different times or moved during the scanning, then a registration type known in the art such as longitudinal registration may be utilized.

At step 404, a visual depiction of the x-ray image is created from data contained in the x-ray image dataset and displayed on a display device. Also displayed on the display device, adjacent to the x-ray image, is an ultrasound image created from the data contained in the ultrasound image dataset. In exemplary embodiments of the present invention, the x-ray data is displayed in a lateral position (e.g., from right to left) and the ultrasound data is displayed in a sagittal position (e.g., from top to bottom). See FIG. 7 for an alternate exemplary embodiment of the present invention that includes a display arrangement with one x-ray view and three ultrasound views within a single display. On the left is the x-ray image 702 with the current location of the user cursor denoted by an arrow within the x-ray image 702. The ultrasound image includes a sagittal view 704 for a particular slice within the ultrasound image with a shadow, or virtual, cursor denoted by an arrow. In addition, the ultrasound image depicted in FIG. 7 includes an axial view 708 and a coronal view 706 of the slice.

Figure 5:
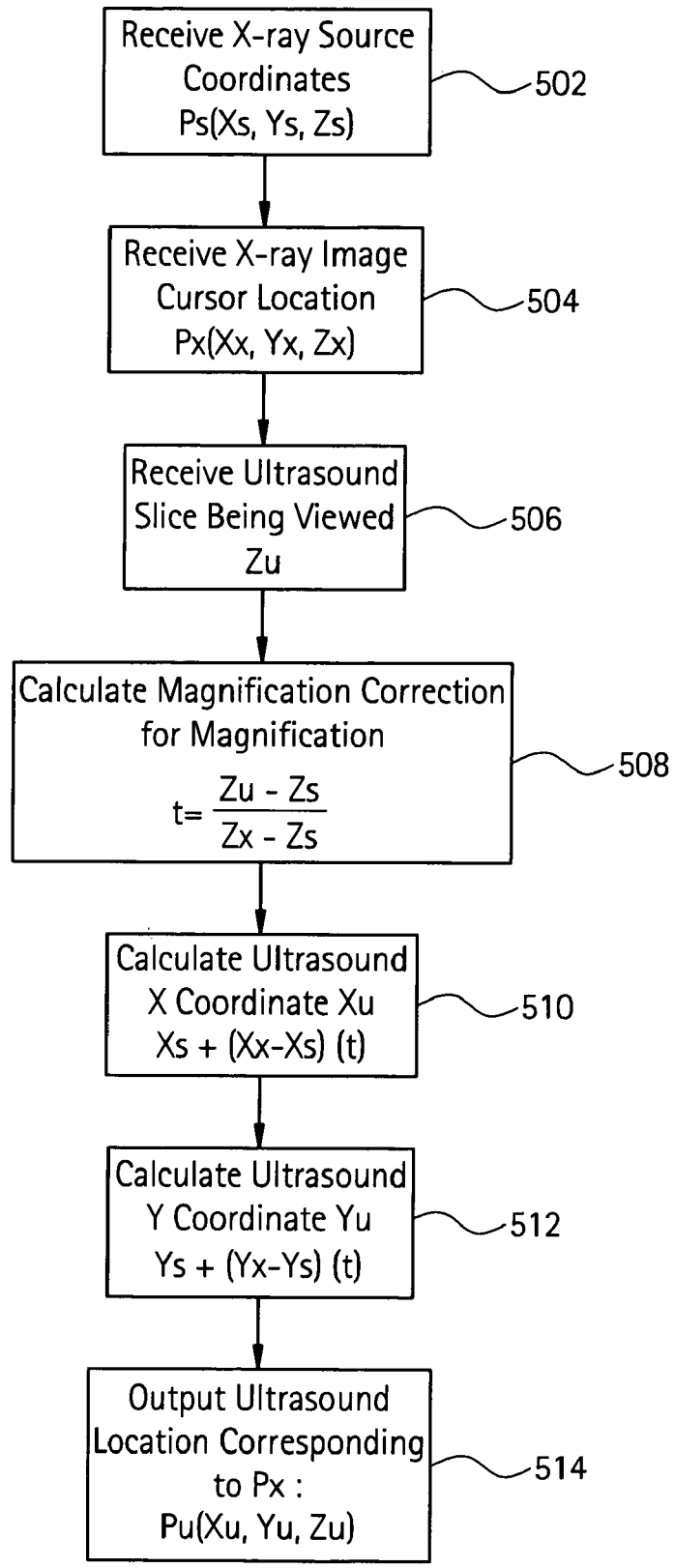
FIG. 5 is a flow diagram of an exemplary calculation for deriving an ultrasound coordinate location based on a x-ray coordinate location.

Referring to step 406 in FIG. 4, a user cursor is detected at a particular location in the x-ray image. In response to detecting the user cursor location, step 408 is performed. In step 408, a linear equation, such as the one described in reference to FIG. 5, is applied to the x-ray image location where the user cursor is located. Inputs to the equation include the particular ultrasound slice being currently viewed as well as the user cursor location in the x-ray image. Applying the linear equation results in a corresponding location in the ultrasound image that has been corrected for magnification.

At step 410, a shadow, or virtual, cursor is moved to the corresponding ultrasound image location. The location of the shadow cursor is visible to the user who is viewing the images on the display. The loop from step 406 through 410 is performed until the user exits out of the images and/or the application. Performing the loop from step 406 through step 410 allows the shadow cursor to move around the ultrasound image in a manner that is simultaneous or nearly simultaneous to the movement of the user cursor in the x-ray image. Alternate exemplary embodiments of the present invention input a user cursor location from an ultrasound image and calculate a corresponding shadow cursor location on an x-ray image.

FIG. 5 is a flow diagram of an exemplary calculation for deriving an ultrasound coordinate location based on an x-ray coordinate location. At step 502, an x-ray source coordinate, Ps, is received. Ps specifies the point in the x-ray coordinate system 306 where the x-ray source is located and is specified as Ps(Xs, Ys, Zs). Next, at step 504, a user cursor location in an x-ray image dataset is received and specified in the x-ray coordinate system 306 as Px(Xx, Yx, Zx). Processing continues at step 506, where the ultrasound slice that the user is viewing or that the user requests to view is received. The ultrasound location corresponding to the x-ray location may be specified as Pu(Xu, Yu, Zu). When the ultrasound slice is specified, the Zu component of the ultrasound location is assigned to the slice value.

Figure 6:
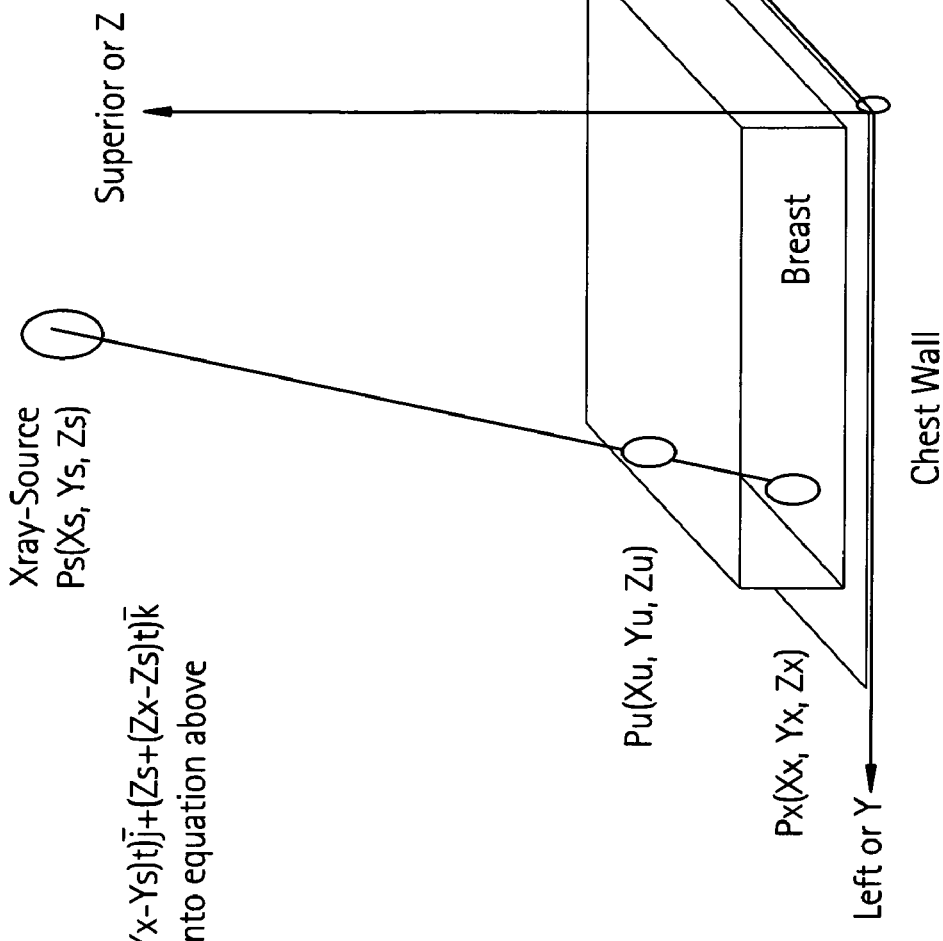
FIG. 6 is a summary of the equations utilized to perform the calculation described in reference to FIG. 5.

Next, at step 508, a magnification correction for the x-ray location is derived based on the data received in steps 502, 504 and 506. In exemplary embodiments of the present invention, the magnification correction may be derived based on the following formula: $t=(Zu-Zs)/(Zx-Zs)$. After the magnification correction is derived, step 510 is performed to calculate the ultrasound coordinate Xu. Xu may be calculated as: $Xs+(Xx-Xs)(t)$. By using the calculation at step 510, the resulting Xu coordinate includes an adjustment for magnification. The Xy coordinate is calculated at step 512 as: $Ys+(Yx-Ys)(t)$. The resulting corresponding ultrasound location, which has been adjusted for magnification, is then output at step 514. In exemplary embodiments of the present invention, the output is to the shadow cursor processing described in reference to FIG. 4. FIG. 6 is a summary of the equations utilized to perform the calculation described in reference to FIG. 5 as well as exemplary derivations of the formulas.

Alternate exemplary embodiments of the present invention include receiving an ultrasound coordinate point from a user cursor and then determining a corresponding shadow cursor location for in an x-ray image. In addition, other types of modalities may be utilized with exemplary embodiments of the present invention and more than one shadow cursor may be created based on receiving the coordinates of a user cursor.

Exemplary embodiments of the present invention have been described in reference to apparatuses and methods for mammography. It should be appreciated, however, that the teachings of the present invention may also be utilized in other areas, such as lung imaging, brain imaging, liver imaging, kidney imaging, bone imaging and other medical areas, as well as in industrial applications, such as detecting low density regions in fabricated parts, or performing fault/fatigue testing (e.g., examining for cracks, depressions, or impurities).

Exemplary embodiments of the present invention may be utilized to more quickly view and compare images collected using different imaging techniques. The use of a linear equation allows the conversion between two or more modalities to be performed quickly and without requiring that large amounts of registration data be stored. Using a linear equation allows the conversion to be performed quickly enough for the shadow cursor and user cursor to appear to be moving simultaneously, or near simultaneously on a display device that is displaying images created from different modalities. In addition, the 3D image (e.g., ultrasound) has the same appearance that it had when it was acquired. This is accomplished while still having a pixel/voxel correspondence mechanism between 3D (e.g., ultrasound) and 2D (e.g., x-ray) images. As described previously, exemplary embodiments of the present invention may be applied to other multi-modality data acquisitions.

As described above, embodiments can be embodied in the form of computer-implemented processes and apparatuses for practicing those processes. In exemplary embodiments, the invention is embodied in computer program code executed by one or more network elements. Embodiments include computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Embodiments include computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

The invention claimed is:

1. A method for multi-modality registration using virtual cursors, the method comprising:
   receiving a two-dimensional image dataset for an object at a first position;
   receiving a three-dimensional image dataset for the object at the first position, said three-dimensional image dataset including a plurality of image slices;
   registering the two-dimensional image dataset with the three-dimensional image dataset without taking into account a magnification factor;
   receiving a user cursor position for a location in the two-dimensional image dataset;
   receiving a slice of interest in said three-dimensional image dataset, said slice of interest selected from said plurality of image slices;
   calculating a shadow cursor position for a location in the three-dimensional image dataset, the shadow cursor position corresponding to the user cursor position and the calculating including a correction for the magnification factor corresponding to the shadow cursor position for the slice of interest; and
   outputting the shadow cursor position.

2. The method of claim 1, further comprising displaying the two-dimensional image dataset on a display device and displaying the slice of interest adjacent to the two-dimensional image dataset on the display device.

3. The method of claim 2, further comprising:
   displaying a user arrow at the user cursor position on the two-dimensional image dataset; and
   displaying a shadow arrow at the shadow cursor position on the slice of interest.

4. The method of claim 1, wherein the two-dimensional image dataset is acquired using an x-ray source and a detector.

5. The method of claim 1, wherein the three-dimensional dataset is acquired using an ultrasound probe.

6. The method of claim 1, wherein said registering is performed during data acquisition.

7. The method of claim 1, wherein said registering includes mechanical registration.

8. The method of claim 1, wherein said registering includes longitudinal registration.

9. The method of claim 1, wherein:
   the three-dimensional image dataset includes ultrasound data;
   the two-dimensional image data set includes x-ray data; and
   the correction for the magnification factor for the slice of interest is derived in accordance with the expression:

$$t=(Zu-Zs)/(Zx-Zs)$$

where Zu is a z coordinate of the slice of interest, Zs is a z coordinate of an x-ray source location and Zx is a z coordinate of the user cursor position.

10. The method of claim 1, wherein:
    the three-dimensional image dataset includes ultrasound data;
    the two-dimensional image data set includes x-ray data; and
    the calculating is performed in accordance the expressions:

$$Xu=Xs+(Xx-Xs)(t)$$

and $$Yu=Ys+(Yx-Ys)(t)$$

where Xu is a x coordinate of the shadow cursor position, Xs is a x coordinate of an x-ray source location, Xx is a x coordinate of the user cursor position, t is the correction for the magnification factor, Yu is a y coordinate of the shadow cursor position, Ys is a y coordinate of an x-ray source location and Yx is a y coordinate of the user cursor position.

11. The method of claim 1, wherein:
    the three-dimensional image dataset includes ultrasound data;
    the two-dimensional image data set includes x-ray data; and the calculating is performed in accordance the expressions:

$$Xu=Xs+(Xx-Xs)(Zu-Zs)/(Zx-Zs)$$

and $$Yu=Ys+(Yx-Ys)(Zu-Zs)/(Zx-Zs)$$

where Xu is a x coordinate of the shadow cursor position, Xs is a x coordinate of an x-ray source location, Xx is ax coordinate of the user cursor position, Yu is a y coordinate of the shadow cursor position, Ys is a y coordinate of an x-ray source location, Yx is a y coordinate of the user cursor position, Zu is a z coordinate of the slice of interest, Zs is a z coordinate of an x-ray source location and Zx is a z coordinate of the user cursor position.

12. A method for multi-modality registration using virtual cursors, the method comprising:
    receiving a two-dimensional image dataset for an object at a first position;
    receiving a three-dimensional image dataset for the object at the first position, said three-dimensional image dataset including a plurality of image slices;
    registering the two-dimensional image dataset with the three-dimensional image dataset without taking into account a magnification factor;
    receiving a slice of interest in said three-dimensional image dataset, said slice of interest selected from said plurality of image slices;
    receiving a user cursor position for a location in the slice of interest in said three-dimensional image dataset;
    calculating a shadow cursor position for a location in the two-dimensional image dataset, the shadow cursor position corresponding to the user cursor position and the calculating including a correction for the magnification factor corresponding to the shadow cursor position; and
    outputting the shadow cursor position.

13. A system for multi-modality registration using virtual cursors, the system comprising:
    a computer system in communication with a first imaging system and a second imaging system, wherein said first imaging system creates a two-dimensional image dataset for an object at a first position, said second imaging system creates a three-dimensional image dataset of the object at the first position, said three-dimensional image dataset including a plurality of image slices, and said computer system includes instructions to implement a method comprising:
    receiving the two-dimensional image dataset from the first imaging system;
    receiving the three-dimensional image dataset from the second imaging system;
    registering the two-dimensional image dataset with the three-dimensional image dataset without taking into account a magnification factor; p1 receiving a user cursor position for a location in the two-dimensional image dataset;
    receiving a slice of interest in the three-dimensional dataset, said slice of interest selected form the plurality of image slices;
    calculating a shadow cursor position for a location in the two-dimensional image dataset, the shadow cursor position corresponding to the user cursor position and the calculating including a correction for the magnification factor corresponding to the shadow cursor position; and
    outputting the shadow cursor position.

14. The system of claim 13 wherein the first imaging system is an x-ray imaging system.

15. The system of claim 14 wherein said x-ray imaging system includes an x-ray source and detector.

16. The system of claim 13 wherein the second imaging system is an ultrasound imaging system.

17. The system of claim 16 wherein said ultrasound imaging system includes an ultrasound probe.

18. The system of claim 13 further comprising a display device in communication with the computer system, wherein said user cursor position is received from said display device.

19. The system of claim 18 wherein said method further comprises displaying the two-dimensional image dataset and the slice of interest adjacent to the two-dimensional dataset on the display device.

20. A computer program product for multi-modality registration using virtual cursors, the product comprising:
    a storage medium readable by a processing circuit and storing instructions for execution by the processing circuit for performing a method comprising:
    receiving a two-dimensional image dataset for an object at a first position;
    receiving a three-dimensional image dataset for the object at the first position, said three-dimensional dataset including a plurality of image slices;
    registering the two-dimensional image dataset with the three-dimensional image dataset without taking into account a magnification factor;
    receiving a user cursor position for a location in the two-dimensional image dataset;
    receiving a slice of interest in said three-dimensional image dataset, said slice of interest selected from said plurality of image slices;
    calculating a shadow cursor position for a location in the three-dimensional image dataset, the shadow cursor position corresponding to the user cursor position and the calculating including a correction for the magnification factor corresponding to the shadow cursor position for the slice of interest; and
    outputting the shadow cursor position.

* * * * *